US00PP17599P2

(12) United States Plant Patent
Michalik

(10) Patent No.: US PP17,599 P2
(45) Date of Patent: Apr. 17, 2007

(54) ***GERANIUM* PLANT NAMED 'PACTAL'**

(50) Latin Name: *Pelargonium×hortorum*
Varietal Denomination: Pactal

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 32 days.

(21) Appl. No.: 11/151,756

(22) Filed: Jun. 14, 2005

(51) Int. Cl.
*A01H 5/00* (2006.01)

(52) U.S. Cl. ..... Plt./329

(58) Field of Classification Search ..... Plt./329
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Zonal *Geranium* plant named 'Pactal', characterized by its upright, rounded and compact plant habit; freely basal branching and flowering habit; leaves without a zonation pattern; red purple-colored flowers with more intense red purple-colored blotches; and good garden performance.

1 Drawing Sheet

Botanical designation: *Pelargonium×hortorum.*
Cultivar denomination: 'Pactal'.

BACKGROUND OF THE INVENTION

The present invention relates to a new and distinct cultivar of Zonal *Geranium* plant, botanically known as *Pelargonium×hortorum,* and hereinafter referred to by the name 'Pactal'.

The new Zonal *Geranium* is a product of a planned breeding program conducted by the Inventor in Dresden, Germany. The objective of the breeding program was to develop new Zonal *Geraniums* with attractive flower coloration.

The new Zonal *Geranium* originated from a cross-pollination made by the Inventor during the summer of 2000 of two unnamed proprietary selections of *Pelargonium×hortorum,* not patented. The cultivar Pactal was discovered and selected by the Inventor as a flowering plant within the progeny from the stated cross-pollination in a controlled environment in Dresden, Germany in June, 2001.

Asexual reproduction of the new cultivar by terminal cuttings in a controlled environment in Dresden, Germany since January, 2002 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Pactal'. These characteristics in combination distinguish 'Pactal' as a new cultivar and distinguish it from the other known Zonal *Geranium* cultivars:

1. Upright, rounded and compact plant habit.
2. Freely basal branching and flowering habit.
3. Leaves without a zonation pattern.
4. Red purple-colored flowers with more intense red purple-colored blotches.
5. Good garden performance.

Plants of the new Zonal *Geranium* differ primarily from plants of the parent selections in flower coloration and flower form.

Plants of the new Zonal *Geranium* can be compared to plants of the cultivar Swero, disclosed in a U.S. Plant Pat. No. 16,752. In side-by-side comparisons conducted in Dresden, Germany, plants of the new Zonal *Geranium* differed from plants of the cultivar Swero in the following characteristics:

1. Plants of the new Zonal *Geranium* were smaller than plants of the cultivar Swero.
2. Plants of the new Zonal *Geranium* had more flowers per umbel than plants of the cultivar Swero.
3. Plants of the new Zonal *Geranium* and the cultivar Swero differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Pactal' grown in a container.

DETAILED BOTANICAL DESCRIPTION

Plants of the cultivar Pactal have not been observed under all possible environmental conditions. The phenotype may vary somewhat with variations in environment, such as temperature and light intensity, without, however, any variance in genotype.

The aforementioned photograph, following observations and averaged measurements describe plants grown during the summer in containers in Dresden, Germany, and under commercial practice in a glass-covered greenhouse with day temperatures about 18° C., night temperatures about 16° C. and light levels ranging from 15 to 100 kilolux. Plants used for the photograph and the description were about nine months old. In the following description, color references are made to The Royal Horticultural Society Colour Chart, 1995 Edition, except where general terms of ordinary dictionary significance are used.

Botanical Classification: *Pelargonium×hortorum* cultivar Pactal.

Parentage:

*Female, or seed, parent.*—Unnamed proprietary selection of *Pelargonium×hortorum,* not patented.

*Male, or pollen, parent.*—Unnamed proprietary selection of *Pelargonium×hortorum,* not patented.

Propagation:

*Type cutting.*—Terminal cuttings.

*Time to initiate roots.*—Summer: About 18 days at 22° C. Winter: About 22 days at 22° C.

*Time to produce a rooted young plants.*—Summer: About 25 days at 22° C. Winter: About 30 days at 22° C.

*Root description.*—Fine, fibrous; white in color.

*Rooting habit.*—Freely branching, dense.

Plant description:

*General appearance.*—Upright, rounded and compact plant habit; uniform; densely foliated.

*Growth and branching habit.*—Moderately vigorous growth habit. Freely basal branching habit with about 15 lateral branches per plant; pinching is not required.

*Plant height, to top of umbels.*—About 30 cm.

*Plants height, to top of foliar plane.*—About 20 cm.

*Plant width.*—About 45 cm.

*Lateral branches.*—Length: About 10 cm. Diameter: About 7 mm. Internode length: About 1 to 2 cm. Texture: Pubescent. Color: 147B.

*Foliage description.*—Arrangement: Alternate or opposite; simple. Length: About 3 to 4 cm. Width: About 5 to 7 cm. Shape: Rounded. Apex: Rounded. Base: Cordate; open. Margin: Bicrenate. Venation pattern: Palmate. Texture, upper and lower surfaces: Slightly pubescent; rough. Color: Developing foliage, upper surface: 146A. Developing foliage, lower surface: 137C. Fully expanded foliage, upper surface: 139A; venation, 146B. Fully expanded foliage, lower surface: 137B; venation, 146B. Zonation pattern: Absent. Petiole: Length: About 4 to 5 cm. Diameter: About 2 mm. Texture, upper and lower surfaces: Pubescent; rough. Color, upper and lower surfaces: 144A.

Flower description:

*Flower arrangement.*—Red purple-colored flowers with more intense red purple-colored splotches; semi-double rotate flowers arranged in rounded hemispherical umbels arising from apical leaf axils. Umbels displayed upright above the foliage on strong peduncles. Flowers face upright to outwardly; flowers slightly cupped and uniform. Flowers persistent. Flowers not fragrant.

*Quantity of flowers.*—Freely flowering habit; about 20 umbels per plant, about 24 flower buds and open flowers per umbel.

*Flowering season.*—Year-round under greenhouse conditions. In the garden in Dresden, Germany, flowering is continuous from April until frost in the fall.

*Flower longevity.*—Individual flowers last about six to ten days and umbels last about three to four weeks on the plant.

*Umbel height.*—About 7 cm.

*Umbel diameter.*—About 10 cm.

*Flower diameter.*—About 4 to 5 cm.

*Flower depth (height).*—About 2 cm.

*Flower buds.*—Length: About 1 cm. Diameter: About 6 mm. Shape: Elliptic. Color: 144A.

*Petals/petaloids.*—Quantity per flower: About seven. Length: About 2.8 to 3 cm. Width: About 2.2 to 2.8 cm. Shape: Roughly spatulate. Apex: Rounded. Base: Attenuate. Margin: Entire. Texture, upper and lower surfaces: Smooth, glabrous; velvety. Color: When opening and fully opened, upper surface: 74B to 74D; blotches, 57A; venation, similar to lamina. When opening and fully opened, lower surface; 75B; towards the base, 75D; venation, similar to lamina.

*Sepals.*—Quantity per flower: About six, arranged in a single whorl. Length: About 1.2 cm. Width: About 2 to 3 mm. Shape: Lanceolate. Apex: Acute. Base: Attenuate. Margin: Entire. Texture, upper and lower surfaces: Pubescent. Color, upper and lower surfaces: 144A.

*Peduncle (umbel stem).*—Length: about 11 to 15 cm. Diameter: About 5 mm. Strength: Strong. Aspect: Upright. Texture: Pubescent. Color: 146B.

*Pedicel (individual flower stem).*—Length: About 2.5 cm. Diameter: About 2 mm. Strength: Moderately strong; flexible. Texture: Sparsely pubescent. Color: 144A.

*Reproductive organs.*—Androecium: Stamen quantity per flower: About twelve. Anther length: About 1 to 2 mm. Anther shape: Oblong. Anther color: Brown. Pollen amount: Sparse. Pollen color: Golden brown. Gynoecium: Pistil quantity per flower: One. Pistil length: About 1 cm. Stigma shape: Five-parted. Stigma color: Red purple. Style length: About 3 to 4 mm. Style color: Red purple. Ovary color: Pale green.

*Seed/fruit.*—Seed and fruit development has not been observed.

Disease/pest resistance: Plants of the new Zonal *Geranium* have not been observed to be resistant to pathogens and pests common to Zonal *Geraniums.*

Garden performance: Plants of the new Zonal *Geranium* have been observed to tolerate rain, wind, and temperatures ranging from −0.5 to 40° C. and have demonstrated good garden performance.

It is claimed:

1. A new and distinct cultivar of Zonal *Geranium* plant named 'Pactal', as herein illustrated and described.

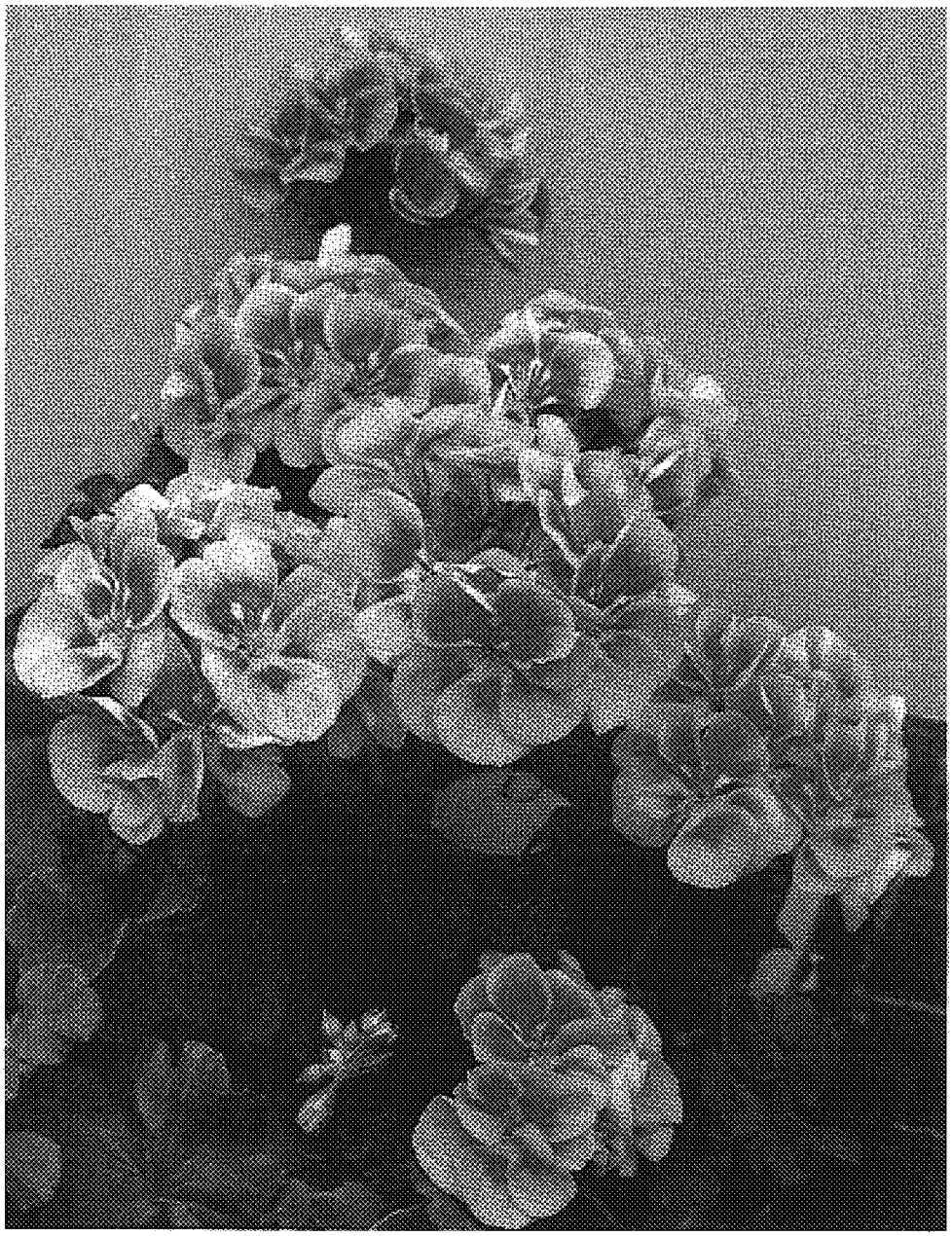

* * * * *